(12) United States Patent
White et al.

(10) Patent No.: US 8,435,243 B2
(45) Date of Patent: May 7, 2013

(54) DISPOSABLE REAMER

(75) Inventors: Patrick M. White, West Chester, PA (US); Gary Victor, Wheatfield, NY (US)

(73) Assignee: Greatbatch Ltd., Clarence, NY (US)

( * ) Notice: Subject to any disclaimer, the term of this patent is extended or adjusted under 35 U.S.C. 154(b) by 176 days.

(21) Appl. No.: 13/025,244

(22) Filed: Feb. 11, 2011

(65) Prior Publication Data

US 2011/0202060 A1    Aug. 18, 2011

Related U.S. Application Data

(60) Provisional application No. 61/303,699, filed on Feb. 12, 2010.

(51) Int. Cl.
*A61B 17/16* (2006.01)

(52) U.S. Cl.
USPC .................................. 606/81; 606/79; 606/80

(58) Field of Classification Search .............. 606/79–81, 606/91, 180; 433/144, 165
See application file for complete search history.

(56) References Cited

U.S. PATENT DOCUMENTS

| | | | |
|---|---|---|---|
| 4,023,572 A | 5/1977 | Weigand et al. | |
| 4,131,116 A * | 12/1978 | Hedrick | 606/81 |
| 5,116,165 A | 5/1992 | Salyer | |
| 5,222,956 A | 6/1993 | Waldron | |
| 5,299,893 A | 4/1994 | Salyer et al. | |
| 5,897,558 A | 4/1999 | Frieze et al. | |
| 5,968,049 A | 10/1999 | Da Rold | |
| 6,001,105 A | 12/1999 | Salyer | |
| 6,221,076 B1 * | 4/2001 | Albrektsson et al. | 606/80 |
| 6,283,971 B1 * | 9/2001 | Temeles | 606/81 |
| 6,730,094 B2 | 5/2004 | Salyer et al. | |
| 6,764,490 B1 * | 7/2004 | Szabo | 606/81 |
| 6,951,563 B2 | 10/2005 | Wolford | |
| 7,217,272 B2 | 5/2007 | Salyer | |
| 2005/0075639 A1 | 4/2005 | Lechot | |
| 2006/0095041 A1 | 5/2006 | Fehlbaum | |
| 2008/0161813 A1 | 7/2008 | Sherry | |
| 2009/0163921 A1 | 6/2009 | Lechot et al. | |

FOREIGN PATENT DOCUMENTS

| | | |
|---|---|---|
| DE | 1566114 | 10/1970 |
| DE | 3934610 | 4/1991 |
| DE | 19532898 | 3/1997 |
| EP | 0893097 | 1/1999 |

(Continued)

OTHER PUBLICATIONS

International Search Report, PCT/IB2007/004126, dated Aug. 7, 2008.

(Continued)

*Primary Examiner* — Todd Manahan
*Assistant Examiner* — Jessica Weiss
(74) *Attorney, Agent, or Firm* — Steven W. Winn

(57) ABSTRACT

A disposable acetabular reamer designed to improve tissue removal efficiency is described. The reamer device comprises a reamer cutting shell and a reamer driver interface. The reamer cutting shell has a hemispherical structure with a plurality of spaced apart rib portions that extend from a central region located about an apex of the shell. A tissue cutting surface further extends along a longitudinal leading edge, trailing edge or both leading and trailing rib portions. The tissue cutting surface further comprises a series of alternating cutting teeth and notches which are bent at a rake angle.

30 Claims, 10 Drawing Sheets

FOREIGN PATENT DOCUMENTS

| | | |
|---|---|---|
| EP | 0947170 | 10/1999 |
| FR | 1031888 | 6/1953 |
| FR | 2233972 | 1/1975 |
| WO | 02/49516 | 6/2002 |
| WO | 02/49517 | 6/2002 |
| WO | 03/030748 | 4/2003 |
| WO | 03/059178 | 7/2003 |
| WO | 03/086208 | 10/2003 |
| WO | 03/092513 | 11/2003 |
| WO | 2004100804 | 11/2004 |
| WO | 2007097749 | 8/2007 |

OTHER PUBLICATIONS

Vendittoli, P.A., A randomised study comparing resection of acetabular bone at resurfacing and total hip replacement, The Journal of Bone & Joint Surgery [Br], Volumn 88-B, No. 8, Aug. 2006.

* cited by examiner

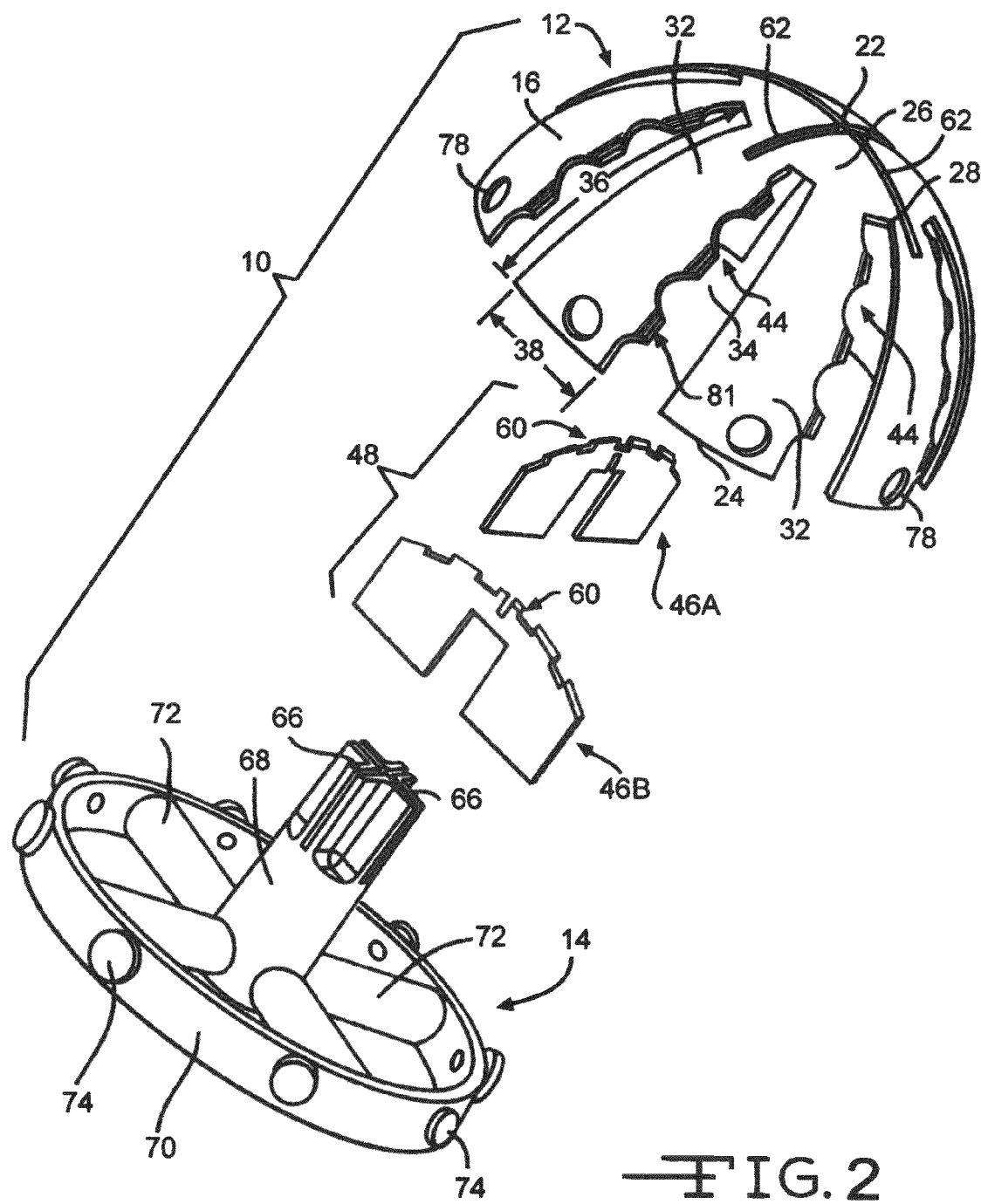

DISPOSABLE REAMER

CROSS-REFERENCE TO RELATED APPLICATIONS

This application claims priority from U.S. Provisional Patent Application Ser. No. 61/303,699, filed Feb. 12, 2010.

FIELD OF THE INVENTION

The present invention relates to the art of orthopedic cutting devices, more particularly, to a reamer device designed to remove tissue from the acetabulum.

PRIOR ART

Reamers are devices intended to remove tissue and bone from the human body. Specifically, the reamer of the present invention is designed to remove tissue from the cotyloid cavity of the acetabulum in preparation for the insertion of a hip joint by a prosthetic cup.

In general, acetabular reamers are constructed with a continuous partially hemispherical surface. This partial hemispherical structure is ideally suited to create a cavity in which to fit a prosthetic cup. Prosthetic cups generally have a curved exterior surface that is inserted into the cotyloid cavity.

A series of discrete tissue cutting openings are typically positioned throughout the outer partially hemisperical surface and extend through the reamer wall thickness. These prior art tissue cutting openings are characteristically designed such that the specific surface that cuts the tissue is provided within the perimeter of the opening.

Many variations of these tissue removing openings have been created, which are generally curved in shape. Other reamers have been designed with "tear drop" or oblong shaped openings. Specific examples of these prior art reamer designs are found in U.S. Pat. Nos. 7,217,272, 6,001,105, and 5,299,893 to Salyer as well as U.S. Pat. No. 6,951,563 to Wolford. In each of these prior art examples, the disclosed reamers embody tissue cutting openings that have a closed perimeter. Furthermore, the tissue cutting surface is enclosed within the perimeter of the opening that lies within the partially hemispherical surface. In other words, the prior art reamers are generally designed with a series of discrete tissue cutting openings. These openings have a continuously closed perimeter with a tissue cutting surface that extends within each opening.

For example, in the '272 patent to Salyer, the disclosed cutting teeth are generally of an oblong shape. The tissue cutting surface is contained within the boundary of the teeth opening. As can be seen in the '272 patent, the tissue cutting surface traverses each opening and is physically bounded by the perimeter of the opening.

In the '105 patent, also to Salyer, the illustrated cutting teeth are generally curved in shape. Similarly to the '272 patent, the tissue cutting surface traverses the width of each opening, and is further contained within the boundary of the tooth opening. The Salyer '893 patent illustrates teeth openings that are generally of a crescent shape. Similarly to the '272 and '105 patents, the tissue cutting surface of the '893 patent is contained within the boundaries of the teeth openings.

The Wolford '563 patent describes a reamer device with cutting teeth openings that are generally of a curved shape. However, unlike the previously described teeth openings attributed to Salyer, the Wolford teeth openings have a raised cutting surface. Although the tissue cutting surface of the '563 patent is not specifically contained within the same surface plane of the opening, the cutting surface is restricted by the dimensions and shape of the discrete opening. The Wolford tissue cutting surface is limited to the relatively small perimeter of the opening. Such a design, as with the previously described Salyer patents, limits tissue contact area. In addition, the relatively small tissue cutting opening of the prior art restricts the flow of debris.

Many problems are associated with these traditional reamer designs. One is that the prior art teeth openings tend to clog with use. As previously mentioned, the prior art reamer tools are generally designed with relatively small openings that restrict the flow of tissue debris. In many cases, a large volume of tissue is excised during a reaming procedure, particularly that of an acetabular reaming procedure. The relatively small prior art teeth openings restrict the flow of debris. The teeth openings clog, thus preventing additional tissue removal and reduce the effectiveness of the cutting tool. As a result, the surgical procedure must be halted for the device to be removed, cleaned and reinserted. Removing and reinserting the reamer increases procedure time and further exposes a person to the possibility of infection.

Another problem is that the tissue cutting surface has a relatively small surface area. As previously described, prior art reamers have been designed with tissue cutting surfaces that generally conform to the dimensions of the bounded teeth openings. Such a design limits the surface area of the tissue cutting surface to being contained within the relatively small perimeter of the opening.

Furthermore, these prior art designs limit the ability of a tool design to incorporate additional tissue cutting surface features. These features include the incorporation of different tissue cutting surface textures as well as the ability to create different tissue cutting surface angles. These prior art design limitations impede tissue removal efficiency. Thus, the use of these prior art reamers results in prolonged surgical times, prolonged patient trauma, increased risk of infection and increased medical costs.

The present invention provides a disposable reamer that incorporates design features which address the limitations of the prior art. The features of the reamer of the present invention provide a cost effective disposable acetabular reamer with increased tissue removal efficiency. Therefore, the reamer of the present invention decreases surgical time, minimizes patient trauma, reduces the possibility of infection and reduces overall medical costs.

SUMMARY OF THE INVENTION

The present invention is an orthopedic reamer designed to cut and remove tissue and bone material. The device is designed to efficiently remove tissue and bone to thereby create a cavity for the insertion of an orthopedic implant. Specifically, the present invention is a reamer that is preferably designed to remove tissue and bone from the acetabulum.

The reamer of the present invention comprises a reamer assembly that connects to a reamer shaft. The reamer assembly further comprises a partially hemispherical shell designed with a series of rib portions that extend longitudinally from a central region about an apex of the shell. These rib portions are attached to a reamer driver interface that provides stability to the reamer assembly. A gap is provided between adjacent rib portions. This feature allows for the unobstructed passage of tissue and contributes to the improved cutting efficiency.

Each rib portion is further designed with a leading edge portion and a trailing edge portion. These leading and trailing edge portions extend longitudinally along opposing sides of each rib. The leading edge portion comprises a tissue and bone cutting surface that extends along a region of the rib portion. This extended tissue cutting surface increases the tissue cutting surface area which enhances the reamer's increased tissue removal efficiency. The tissue cutting surface further incorporates various cutting surface textures, such as a serrated edge, or razor thin edge, among others.

Furthermore, the tissue cutting surface can be bent, thereby providing a customizable rake angle that increases the tissue and bone cutting efficiency of the present reamer.

Therefore, the features of the reamer of the present invention provide for a reamer with increased tissue removal efficiency as compared to the prior art. Thus, a reduction in surgical procedure time, patient trauma, infection risk and associated medical costs is achievable.

SUMMARY OF THE DRAWINGS

FIG. 2 is an exploded view illustrating the internal components of the reamer of the present invention.

DETAILED DESCRIPTION OF THE INVENTION

Figure 1:
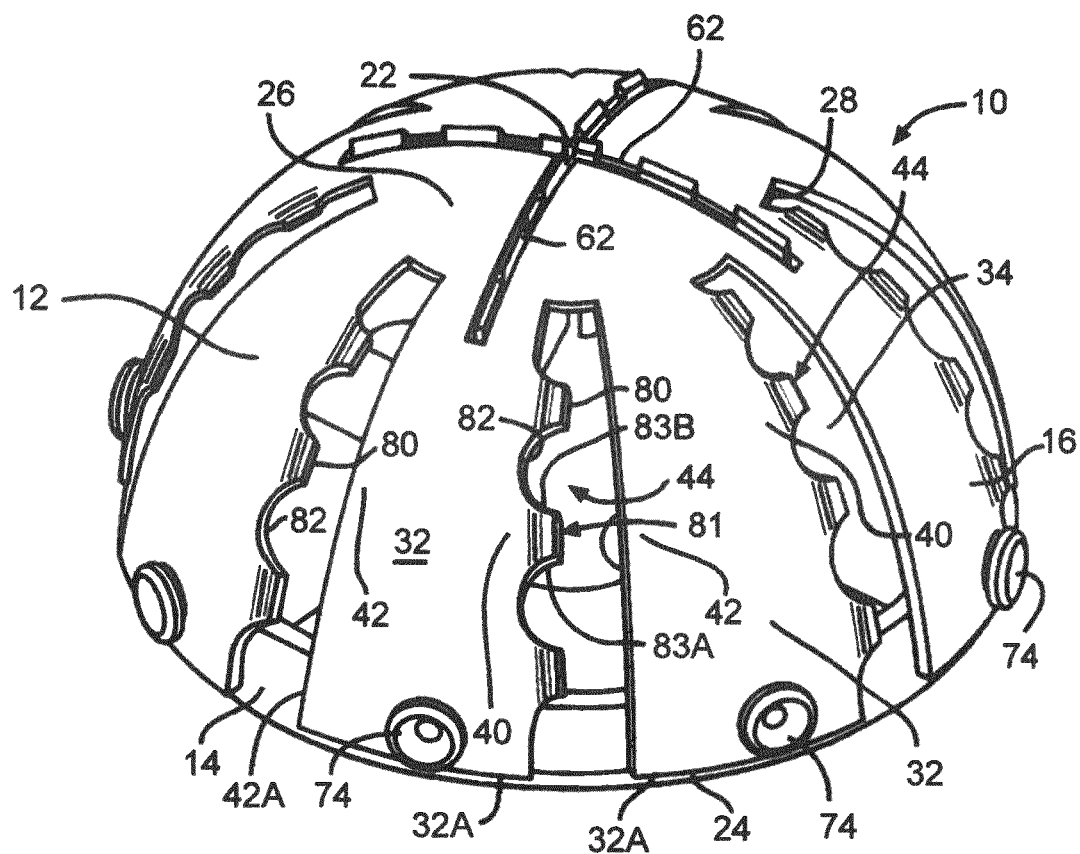
FIG. 1 is a perspective view of the reamer of the present invention.

Now turning to the figures, FIG. 1 illustrates a preferred embodiment of a reamer 10 of the present invention. As illustrated, the reamer 10 preferably comprises a cutting shell 12 that is in communication with a reamer drive interface 14. The reamer drive interface 14 provides strength and rigidity to the cutting shell 12. In addition, the reamer drive interface 14 provides a means for connecting a drive shaft (not shown) to the reamer 10. Thus, when the reamer 10 is connected to the drive shaft (not shown) a physician can operate the reamer 10 from a distal location. The reamer 10 can either be manually operated or, alternatively, be connected to a motor (not shown) to provide power assisted tissue removal.

Figure 5:
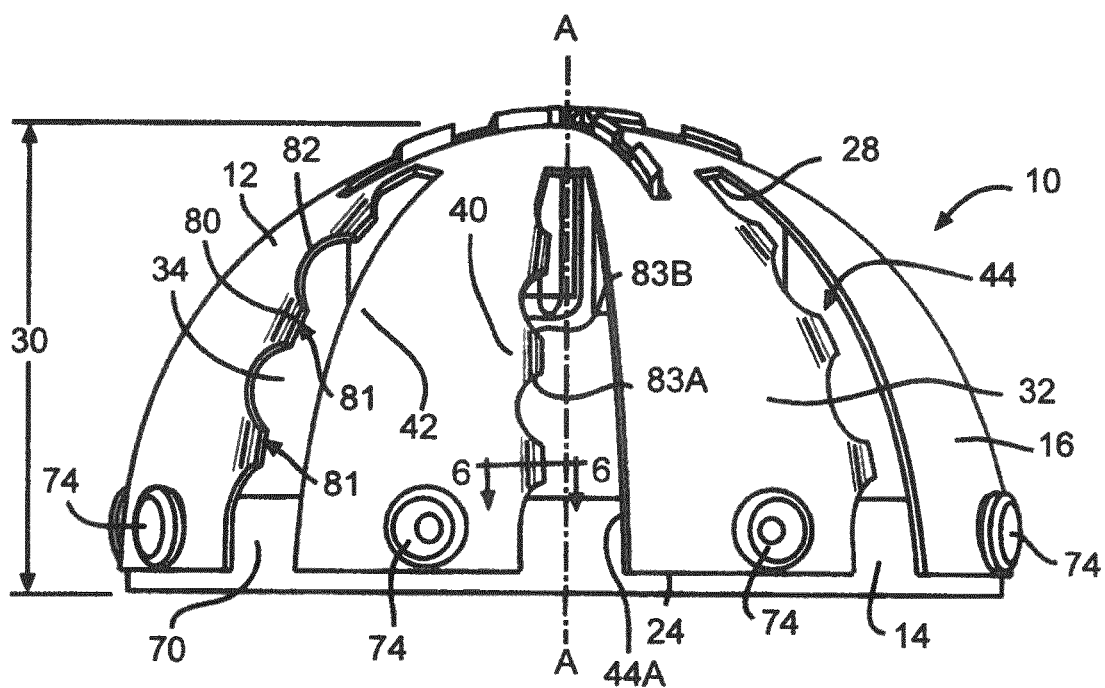
FIG. 5 is a side view of the reamer of the present invention.
Figure 8:
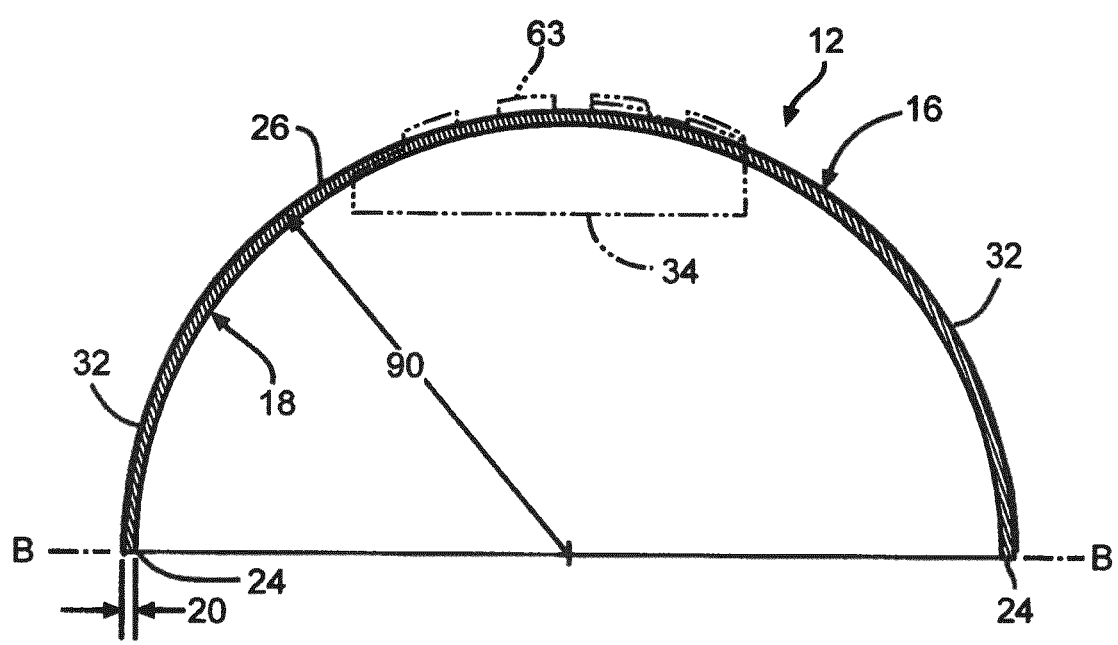
FIG. 8 is an enlarged cross-sectional view along line 8-8 of FIG. 7 illustrating a portion of the cutting shell 12 of the present reamer.

As illustrated in FIG. 1, the cutting shell 12 is generally of a hemispherical shape. The shell 12 further comprises an exterior surface 16, an interior surface 18 (FIG. 8) and a wall thickness 20 therebetween (FIG. 8). In a preferred embodiment, the wall thickness 20 ranges from about 0.5 mm to about 2 mm. The shell 12 has a curvature that comprises at least a portion of a hemisphere extending from an apex 22 to a lower edge 24 located about at an equator of a full hemisphere. In a preferred embodiment, cutting shell 12 is rotatable about a longitudinal axis A-A (FIG. 5).

The present reamer 10 comprises a central region 26 located at a distal portion of the shell 12 adjacent to the apex 22. The central region 26 is, but not all the way to, a hemispherically curved surface that extends from the apex 22 toward the lower edge 24. In that respect, the central region 26 extends to an imaginary plane perpendicular to the longitudinal axis A-A that is from about 10 percent to about 60 percent of the distance from the apex 22 to the lower edge 24. The central region 26 has a continuous surface with a preferred diameter from about 20 mm to about 80 mm.

In a preferred embodiment, the shell 12 has an annular perimeter at the lower edge 24 having a diameter from about 20 mm to about 80 mm. The shell 12 also has a shell height 30 that extends from the lower edge 24 to the apex 22 (FIG. 5). It is preferred that the height 30 range from about 10 mm to about 50 mm.

A plurality of rib portions 32 extend from the central region 26 to the lower edge 24 of the cutting shell 12. In a further preferred embodiment, the plurality of rib portions 32 extend from the intermediate edge 28 of the central region 26 to respective lower edges 32A which cumulatively form the lower edge 24 of the shell 12. Each rib portion 32 is spaced apart from an adjacent rib 32 by a gap 34 therebetween. The rib portions 32 are further characterized by a longitudinal rib length 36 that extend in a longitudinal manner from the intermediate edge 28 of the central region 26 of the shell 12 in a similar manner as the longitudinal lines on a globe. In addition, the rib portions 32 have a lateral rib width 38 (FIG. 2). A leading edge portion 40 and a trailing edge portion 42 further comprise each rib portion 32 of the shell 12. The leading and trailing edges 40, 42 extend along opposite sides of the length 36 of each rib portion 32.

In a preferred embodiment, a tissue cutting surface 44 is provided along a portion of the leading edge 40. The leading edge 40 provides an extended tissue cutting surface 44 that contributes to the device's tissue removal efficiency. In an alternately preferred embodiment, a secondary tissue cutting surface 42A extends along a portion of the trailing edge 42. Alternatively, the tissue cutting surfaces 44, 42A can extend along a portion of both the leading and trailing edges 40, 42.

FIG. 2 illustrates the components that comprise the reamer 10 of the present invention. As previously mentioned, the reamer 10 comprises a cutting shell 12 and a reamer drive interface 14. Two standoffs 46A, 46B preferably connect with the reamer drive interface 14 and the cutting shell 12. These standoffs 46A, 46B are designed to fit together in a perpendicular orientation to create a standoff base 48. The standoff base 48 provides an interface between the cutting shell 12 and reamer driver interface 14. Alternatively, the standoffs 46A, 46B are not necessarily perpendicularly oriented. It is contemplated that the standoffs 46A, 46B could be oriented at angles other than 90° such that they connect between the cutting shell 12 and drive interface 14. It is further contemplated that a single standoff 46A or 46B or, alternatively, a plurality of standoffs 46A and 46B can be provided between the driver interface 14 and reamer shell 12.

Figure 3A:
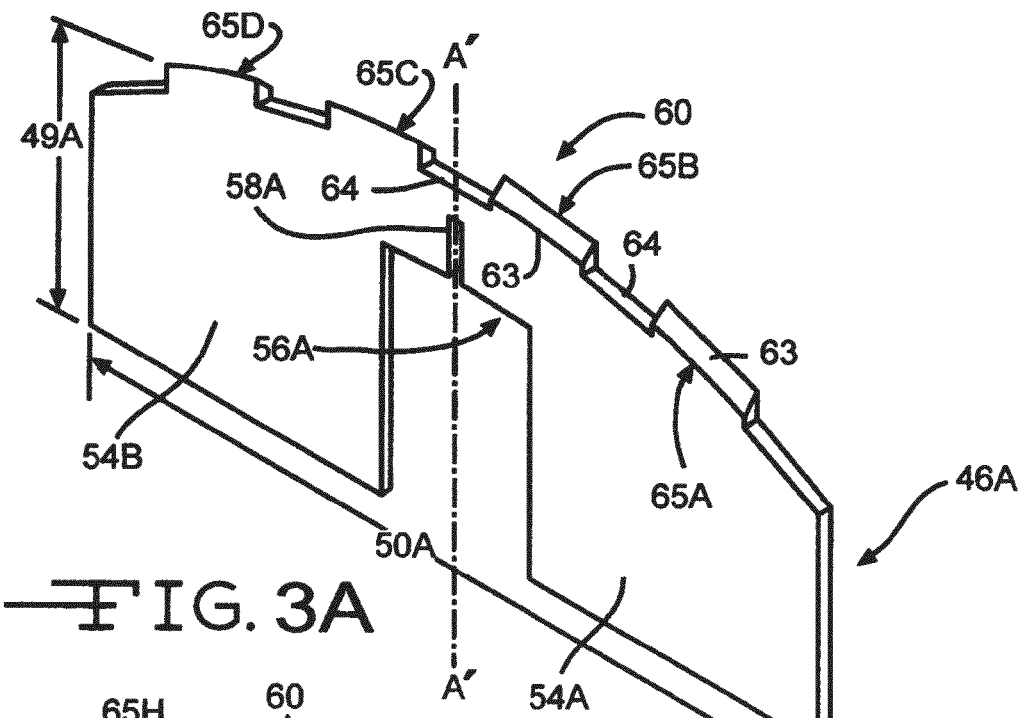
FIGS. 3A and 3B are enlarged perspective views illustrating embodiments of standoffs 46A, 46E of the present reamer.
Figure 3B:
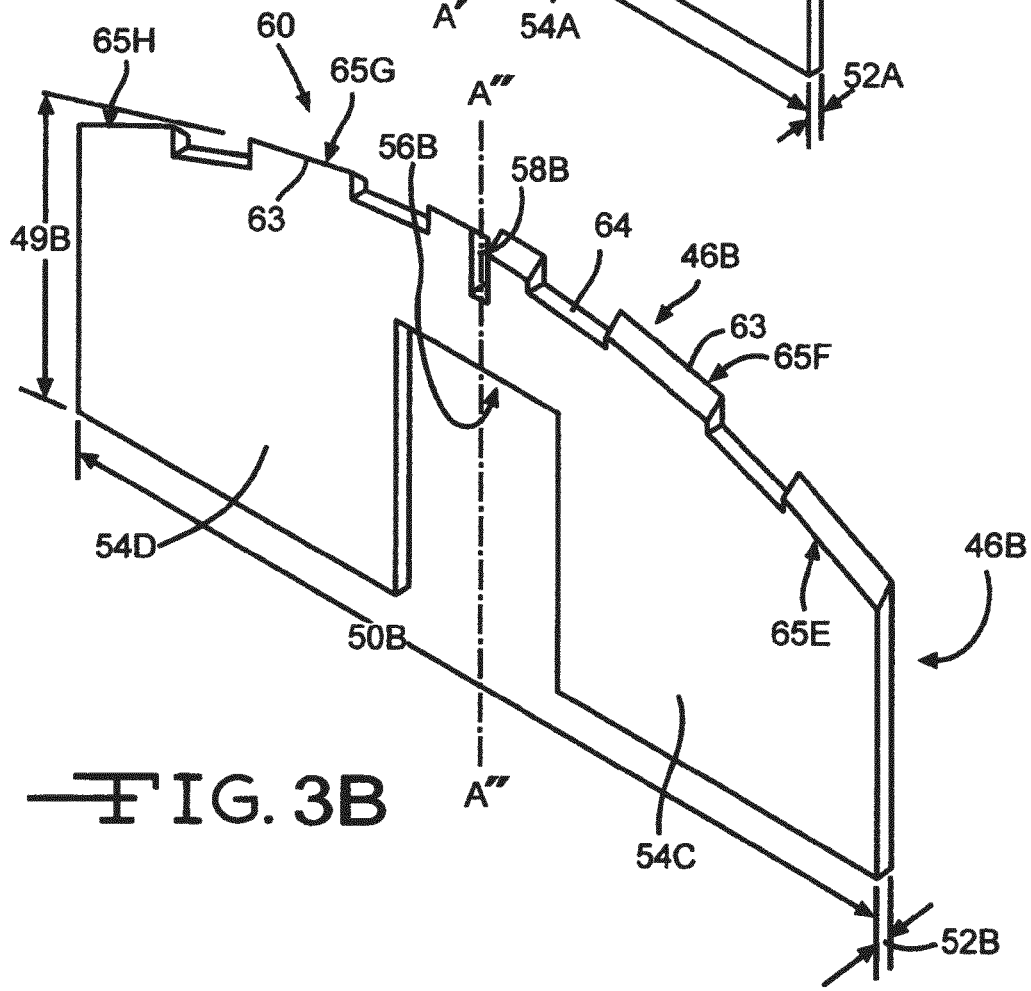

FIGS. 3A and 3B illustrate enlarged views of the first standoff 46A and the second standoff 46B. Each standoff 46A, 46B comprises a standoff height 49A, 49B, a standoff width 50A, 50B and a standoff wall thickness 52A, 52B. The first standoff 46A comprises two leg portions 54A, 54B, with an archway 56A therebetween. Similarly, the second standoff 46B comprises two leg portions 54C and 54D with an archway 56B therebetween. A first slit 58A is positioned through a bottom portion of the archway 56A of the first standoff 46A. The second standoff 46B comprises a second slit 58B that is positioned through a top portion of its archway 56B. In a preferred embodiment, the first slit 58A of the first standoff 46A interfaces with the second slit 58B of the second standoff 46B, thereby creating the standoff base 48 (FIG. 2).

A standoff tissue cutting surface 60, located at a distal standoff portion, preferably spans each standoff width 50 along the topside of the standoff 46A, 46B as shown in FIGS. 3A and 3B. In a preferred embodiment, the standoff tissue cutting surface 60 has a serrated edge. As shown in FIGS. 3A and 3B, the serrated tissue cutting surface 60 of each standoff 46A, 468 comprises alternating teeth 63 and notches 64. In a further preferred embodiment, teeth surfaces 65A-H, are diametrically opposed about their respective longitudinal axes A'-A' and A"-A". As shown in FIG. 3A, teeth surfaces 65A and 65B are oriented 180° about axis A'-A' from teeth surfaces 65C and 65D. Similarly as shown in FIG. 3B, teeth surfaces 65E and 65F, and teeth surfaces 65G and 65H are positioned in opposing orientations about axis A"-A". When assembled together in the standoff base 48, axes A'-A' and A"-A" become parallel to axis A-A.

Alternatively, the standoff tissue cutting surface 60 may be designed with a thin "razor" edge. In this alternate embodiment, a "razor" edge is defined herein as having opposing angled standoff side wall thicknesses 52 such that an edge, capable of cutting tissue, is formed at the topside of the standoff 46A, 46B. When assembled, the standoff base 48 preferably comprises cutting surfaces 60 that are perpendicularly oriented.

In a preferred embodiment, the cutting surface 60 of the standoff base 48 is positioned through corresponding shell slits 62 (FIGS. 1 and 2). These slits 62 extend through the wall thickness 20 of the central region 26 and partially into some, but not necessarily all, of the rib portions 32 of the cutting shell 12. The shell slits 62 are preferably sized and dimensioned to allow the standoff cutting surface 60 to pass through. When the reamer 10 of the present invention is inserted into a patient, the standoff cutting surfaces 60 are designed to initiate a cut into the targeted tissue.

Figure 4:
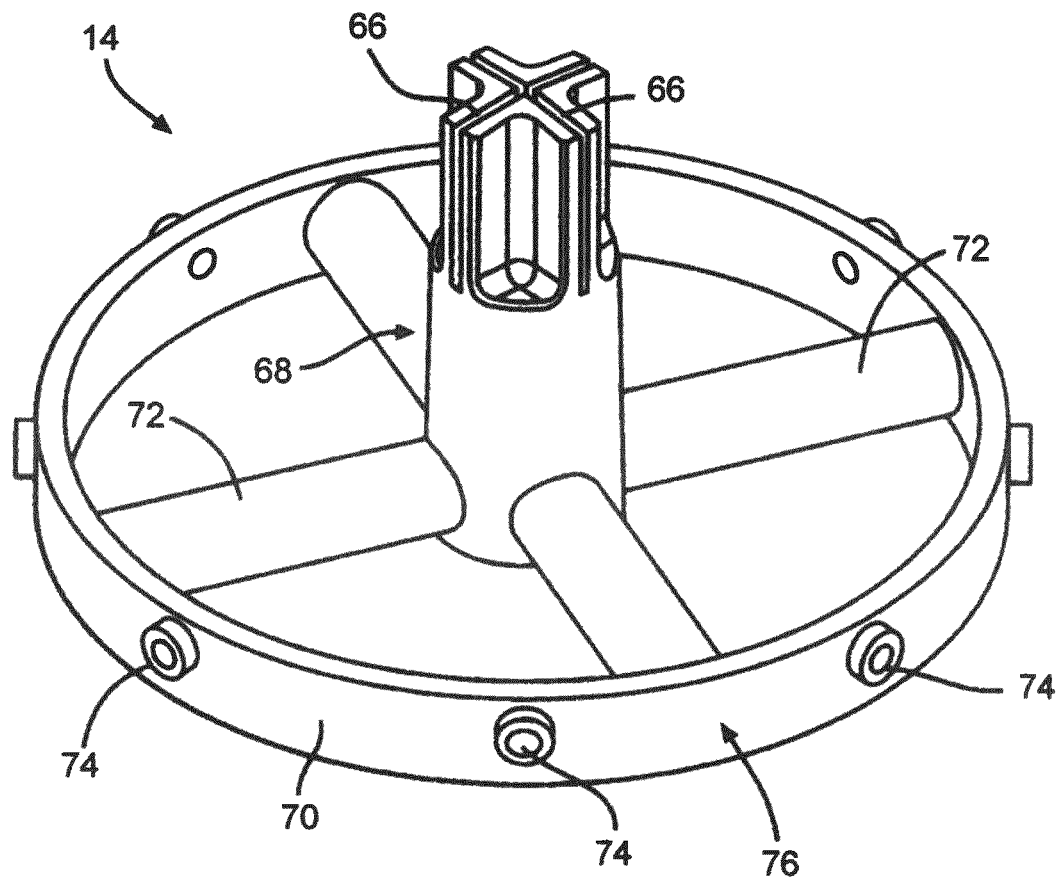
FIG. 4 is an enlarged perspective view of an embodiment of a reamer driver interface 14 of the present invention.

An enlarged view of the reamer driver interface 14 is illustrated in FIG. 4. The interface 14 comprises a band 70 that surrounds a plurality of struts 72, and a pedestal 68, as illustrated. The reamer driver interface 14 preferably has a curved diameter and provides support for the reamer 10 of the present invention. In a preferred embodiment, the diameter of the interface 14 is dimensioned similarly to that of the cutting shell base 24. Such a preferred embodiment encourages a snug interference fit between cutting shell 12 and interface 14.

It is preferred that the pedestal 68 be positioned in a central area that is encircled by the band 70. Struts 72 are preferably positioned in a perpendicular orientation about the pedestal 68. These struts 72 are designed to provide structural support for the driver interface 14 and also provide a means of attachment for the reamer shaft (not shown). In a preferred embodiment, two struts 72 are positioned through a portion of the pedestal 68 in a perpendicular orientation. In an alternatively preferred embodiment, four struts 72 are positioned in a perpendicular relationship about the pedestal 68. In either preferred embodiment, the pedestal 68 is located securely about the central region of the driver interface 14. Although preferred, struts 72 do not necessarily need to be orientated perpendicularly to each other.

It is contemplated that driver interface 14 could be constructed without the pedestal 68 and standoffs 46A, 46B. Such an alternative embodiment could comprise a reamer driver interface 14 comprising either a single strut 72, a plurality of struts 72, a bar and boss (not shown), or a ring-and-strut combination (not shown) spanning the diameter of the interface 14. It is also preferred that the interface 14 be made from a biocompatible material. Preferred biocompatible materials include, but are not limited to, poly(etheretherketone) (PEEK), acrylonitrile butadiene styrene (ABS), stainless steel, and titanium.

The leg portions 54A, 54B and 54C, 54D, located at proximal portions of respective standoffs 46A, 46B, are designed to fit into a series of pedestal slots 66 comprising the drive interface 14 (FIGS. 2 and 4). These slots 66 are preferably formed into a centrally positioned pedestal 68. Leg portions 54A, 54B are inserted into the pedestal slots 66 establishing a tight fit therebetween. The pedestal slots 66 are designed to provide rigid structural support that holds the standoff base 48 together. Furthermore, the pedestal slots 66 contribute to the structural support between standoffs 46A, 46B and cutting shell 12 of the present invention. In a preferred embodiment, the size of the openings of the pedestal slot 66 corresponds to the width of the leg portions 54A, 54B and 54C, 54D of the respective standoffs 46A, 46B.

In a preferred embodiment, standoffs 46A, 46B are made from a biocompatible material such as a biocompatible polymer or metal. These biocompatible materials include, but are not limited to, poly(etheretherketone) (PEEK), acrylonitrile butadiene styrene (ABS), stainless steel, and titanium. These preferred biocompatible materials are desirable because they are lightweight, are cost effective and provide structural rigidity. It is further preferred that the standoff height range from about 5 mm to about 20 mm and the standoff width 50 range from about 10 mm to about 50 mm.

In a preferred embodiment shown in FIG. 4, struts 72 are cylindrical in shape with a cross-sectional diameter from about 3 mm to about 8 mm. Alternatively, struts 72 can be fabricated with various cross-sectional shapes including, but not limited to, rectangular, octahedral, or triangular. It is preferred that the length of the struts 72 be made such that they span the diameter of the interface 14. Alternatively, the strut 72 can be designed to compress against the wall of the pedestal 68 to provide a snug fit between the pedestal 68 and interface band 70.

In a preferred embodiment, a series of studs 74 are positioned along the exterior surface 76 of the interface band 70. These studs 74 are dimensioned such that they mate with corresponding holes 78, positioned at the proximal portion of the ribs 32. In a preferred embodiment, studs 74 are placed through holes 78 of the reamer shell 12, providing a rigid connection therebetween (FIGS. 1 and 5).

The reamer 10 is preferably sized to allow access to tissue in and around the acetabulum. Alternatively, the reamer 10 can also be sized and dimensioned to allow access to other tissue areas. For example, reamer 10 can be used to remove tissue in and around fingers, toes or shoulder area if desired.

As previously mentioned, a gap 34 is provided between adjacent rib portions 32. This gap 34 provides an open passageway for the unobstructed flow of debris. In a preferred embodiment, gap 34 is dimensioned to allow debris of varying sizes to easily pass through. The gap 34 is bounded by the leading edge 40 on one side and by the trailing edge 42 on the opposite side. The gap 34 is further bounded by the interface band 70 on the bottom side and by the intermediate edge 28 of the central region 26.

It is preferred that the gap 34 generally be of a rectangular shape with a longitudinal length extending from about 10 mm to about 40 mm and a latitudinal width extending from about 2 mm to about 10 mm. Alternatively, the gap 34 is not necessarily of a rectangular shape and may take the shape of a multiple of forms. For example, the gap 34 may be triangular or crescent form.

As shown in FIGS. 1, 2, 5 to 7, in a preferred embodiment, the tissue cutting surface 44 is comprised of a series of alternating reamer teeth 80 and notches 82 that extend along a portion of the leading edge 40. Preferably, a notch 82 having a radius of curvature from about 1 mm to about 5 mm, is located adjacent a reamer tooth 80 having a width and height from about 1 mm to about 5 mm. Although it is preferred that the tissue cutting surface 44 is provided along a portion of the leading edge 40, it is contemplated that a secondary tissue cutting surface 44 may also be provided along a portion of the trailing edge 42. Alternatively, the tissue cutting surface 44 may be provided along a portion of both the leading and trailing edges 40, 42. This alternative embodiment allows for efficient tissue removal in either clockwise or counter clockwise as the reamer 10 rotates about longitudinal axis A-A.

Figure 6:
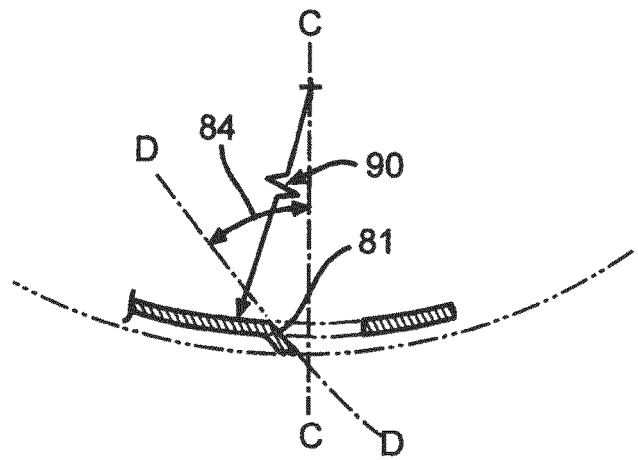
FIG. 6 is an enlarged cross-sectional view along line 6-6 of FIG. 5 illustrating an embodiment of the reamer teeth 80 of the present invention.

In a preferred embodiment, reamer teeth 80 are bent outwards, extending away from the exterior surface 16 of the shell 12. Furthermore, these reamer teeth 80 are bent such that they do not lie in the same hemispherical curvature plane of the shell 12. Bending the reamer teeth 80 outwards, as shown in the preferred embodiment of FIGS. 5 and 6, provides for a rake angle 84. A preferred embodiment of a positive rake angle 84 is illustrated in FIG. 6. A positive rake angle 84 is preferred because it further increases tissue removal efficiency. The positive rake angle 84 enables the reamer teeth 80 to "bite" into the tissue, creating a reamed cavity with a smooth surface. This smooth surface is desirable because it allows for a secure implant fit. A smooth reamed surface also reduces physical wear of an implant (not shown) which increases the implant's service life and reduces the need for additional implant replacement surgeries.

Referring to FIGS. 1, 2, 5-7 and 9, although the reamer cutting surface 81 of the reamer teeth 80 appears flat, the cutting surface 81 is of a partially hemispherical surface. Each reamer tooth 80 cuts a sector of a portion of a hemisphere that approaches the cutting radius. The cutting teeth 80 comprises two buttress portions 83A, 83B extending from the cutting shell 12 and meeting an intermediate cutting edge curvature, the cutting surface 81, as a line segment of a second hemisphere, wherein the line segment comprises a continuum of cutting edge radii, each radii originating at the spherical center with a second imaginary hemisphere that is greater than the first hemisphere of the cutting shell 12 and wherein the plurality of cutting teeth 80 are rotatable about the longitudinal axis A-A. In other words, at least one of the reamer cutting teeth 80 comprises a cutting edge or cutting surface 81 having a curvature as a line segment comprises a continuum of cutting edge radii, each radii originating at the spherical center of the hemisphere of the cutting shell 12 and wherein the plurality of cutting teeth 80 are rotatable about the longitudinal axis A-A.

Furthermore, the smooth reamed cavity allows for the implant (not shown) to move with limited resistance. This ability to move with limited resistance, increases patient mobility and minimizes discomfort. This rake angle 84 feature can be customized for different tissue removal requirements. The teeth 80 of the reamer 10 can be fabricated with a uniform rake angle 84 or alternatively, the reamer 10 can be fabricated with multiple rake angles 84.

The rake angle 84 is defined herein as the angle between axis C-C, which is perpendicular to the longitudinal axis A-A, and line D-D which is tangent to tooth cutting surface 81. As shown, perpendicular axis C-C intersects the leading most point of the tooth cutting edge surface 81. Line D-D, tangent to the tooth cutting surface 81, intersects perpendicular axis C-C forming the rake angle 84 therebetween. It is preferred that rake angle 84 range from about 5° to about 45°.

Figure 7:
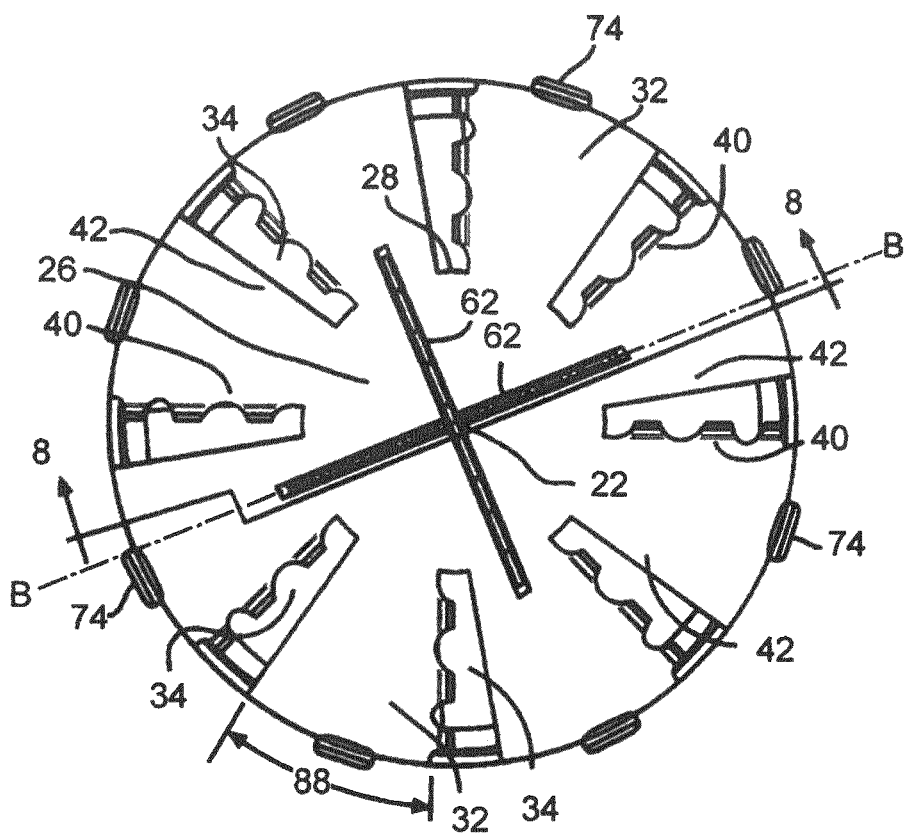
FIG. 7 is a top view of the reamer of the present invention.

Referring now to FIG. 7, in a preferred embodiment, rib portion 32 has a tapered rib width 88. The tapered width 88 gradually widens as it extends from the central region 26 of the shell 12 to lower edge 24 at the interface band 70. It is preferred that the lateral width 88 of each rib 32 ranges from about 2 mm to about 30 mm. Alternatively, rib portion 32 can be fabricated with a constant lateral width 88.

Figure 9:
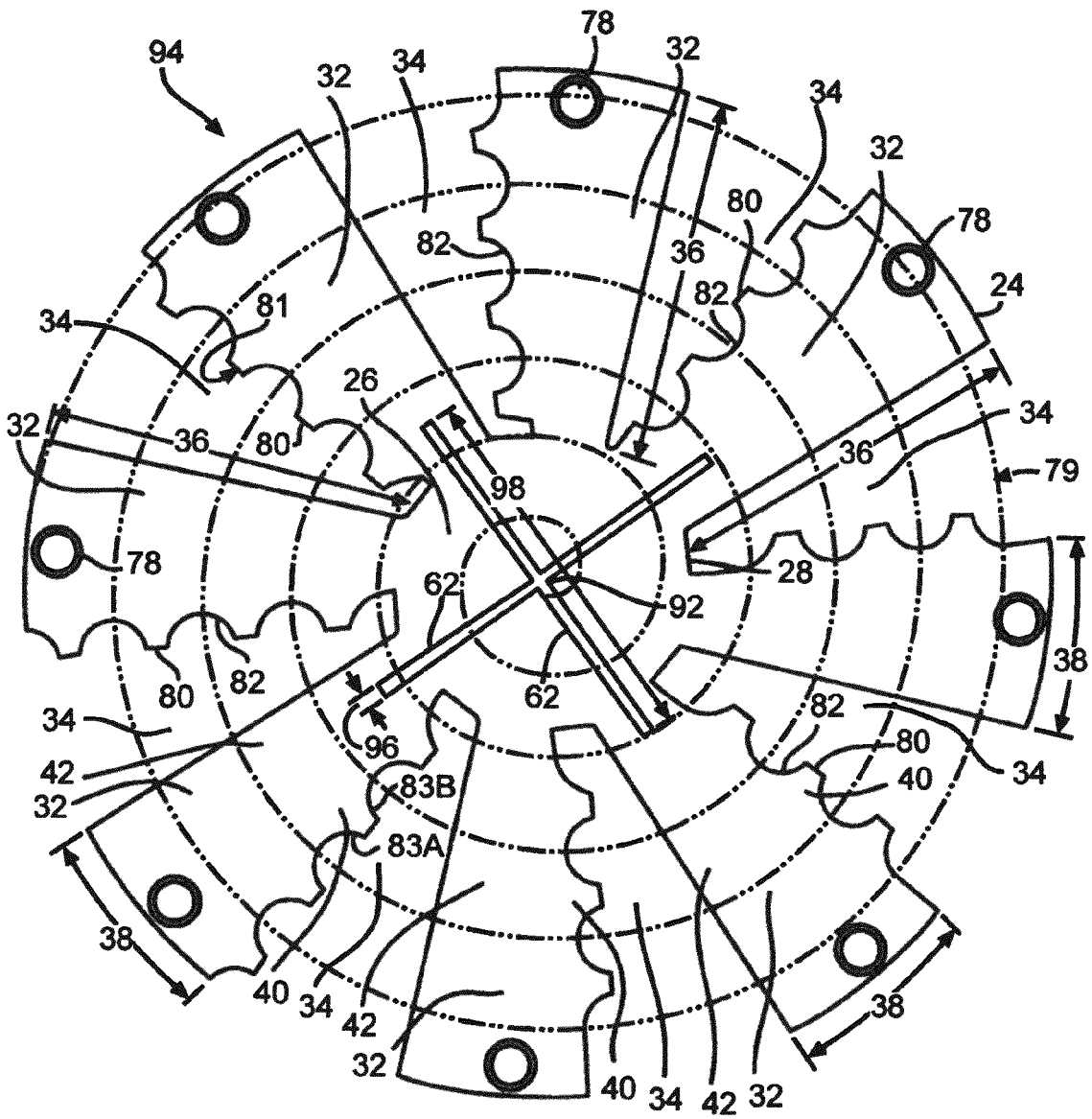
FIG. 9 is a top view of an embodiment of a fabricated disc 94 of the present reamer.

As previously mentioned, an opening 78 is positioned through a distal portion of the rib portion 32 (FIGS. 2 and 9). The opening 78 is designed to fit over stud 74 and provide a secure bond between the shell 12 and the reamer drive interface 14 therebetween. The opening 78 is dimensioned such that each stud 74 is placed through opening 78. During the assembly process, studs 74 are heated thereby increasing their diameter to a dimension somewhat greater than that of the opening 78. A tight interference bond between studs 74 and opening 78 is established. It is preferred that studs 74 be composed of a biocompatible material. Preferred biocompatible materials include, but are not limited to, poly(etheretherketone) (PEEK), acrylonitrile butadiene styrene (ABS), stainless steel, and titanium.

FIG. 8 illustrates a cross-sectional view along line 8-8 of the reamer shell 12 of the present invention shown in FIG. 7. This cross-sectional view illustrates a portion of the hemispherical reamer shell 12 of the present invention. The figure illustrates the perspective as if the shell 12 were sliced along lateral axis B-B from the central region 26 through to the lower edge 24 of diametrically opposed rib portions 32. The cross-sectional view illustrates the preferred curved exterior surface 16 and interior surface 18. As shown, the preferred radius 90 of the reamer shell 12 of the present invention is from about 10 mm to about 40 mm.

The manufacturing process of the reamer 10 begins with the fabrication of the desirable cutting features into a planar disc 94 as previously described. The disc 94, as illustrated in FIG. 9, preferably has a planar surface. In a preferred embodiment, the diameter of the disc 94 is from about 20 mm to about 100 mm. In a preferred embodiment, the disc 94 is composed of a biocompatible metal that includes but not limited to stainless steel, titanium and MP35N.

As illustrated in FIG. 9, disc 94 has been fabricated with the features of the present invention as previously described. The disc 94 comprises the central region 26 that radially extends from a central point 92. The central point 92 of the disc 94 is the apex 22 of the cutting shell 12 once the disc 94 is formed into the cutting shell 12. As FIG. 9 shows, material has been removed from the disc 94, forming the rib portions 32 that are separated by gaps 34. These rib portions 34 extend from the intermediate edge 24 of the central region 24 to their respective lower edges 24. The tissue cutting surface 44 has been formed into a portion of the leading edge 40.

In the featured embodiment illustrated in FIG. 9, the notches 82 between teeth 80 of the serrated cutting surface 44 of the rib portion 32 are aligned in a spiral orientation as indicated by dashed line 79. This spiral orientation ensures the cutting teeth 80 cover a greater tissue surface area, thereby maximizing the amount of tissue removed and minimizing cutting resistance of the reamer teeth 80. As illustrated in FIG. 9, dashed line 79 is shown such that it traverses through the center of notch 82. Alternatively, spiral dashed line 79 could also be illustrated traversing through the center of cutting teeth 80. In either case, it is preferred that the cutting teeth 80 be aligned in a spiral orientation.

It is preferred that the disc 94 be designed with reamer slots 62 that extend through the wall thickness 20 of the central region 26 of the shell 12. As shown in FIG. 7, these reamer slots 62 are preferably sized to allow the passage of the standoff tissue cutting surface 60. In a preferred embodiment, these reamer slots 62 have a rectangular shape with a slot width 96 of about 1 mm to about 3 mm and a slot length 98 from about 10 mm to about 60 mm. It is also preferred that these slots 62 be arranged in a perpendicular orientation to each other to allow the tissue cutting surface 60 of the standoff base 48 to pass through. It is further preferred that a portion of the reamer slot 62 extend past the intermediate edge 28 of the central region 26 and into a portion of the rib 32. This feature further maximizes tissue removal by contacting a greater surface area. Alternately, the disc 94 may comprise a series of holes (not shown) that are positioned throughout the center region 26. These central region holes (not shown) provide an alternative tissue cutting surface that initiates tissue removal.

Figure 10:
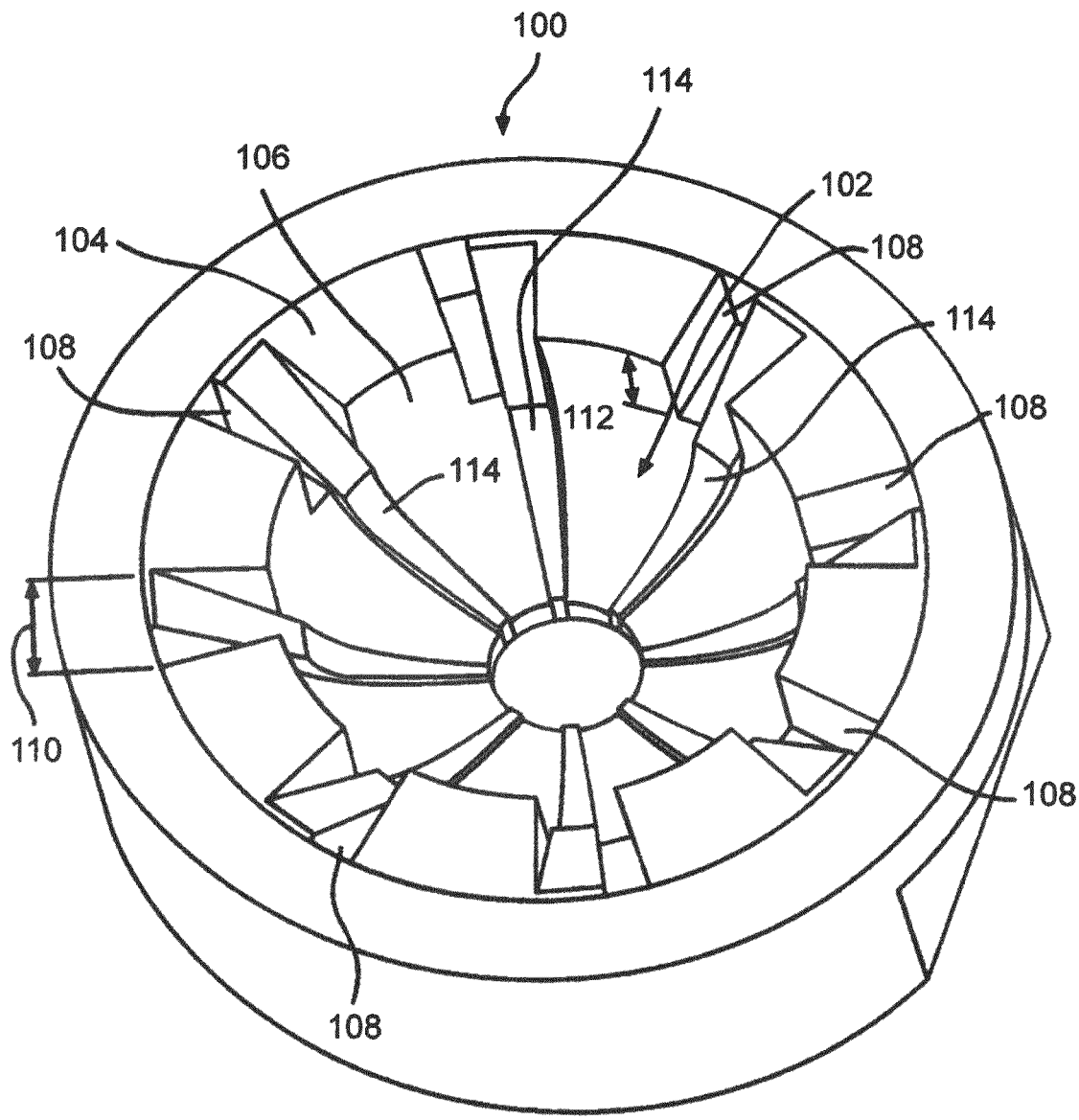
FIG. 10 is a perspective view of a preferred embodiment of a mold 100 for manufacturing the present reamer.

FIG. 10 illustrates a mold 100 that is used during the assembly process of the reamer 10. The mold 100 comprises a body with a compound cavity 102 consisting of a primary cavity 104 and a secondary cavity 106. As illustrated, the primary cavity 104 fluidly transitions into the secondary cavity 106 with increasing depth into the mold 100. The secondary cavity 106 is located furthest into the depth of the mold 100 and has a generally curved bottom. The secondary mold cavity 106 preferably has a diameter from about 20 mm to about 80 mm. The secondary cavity 106 is dimensioned to impart the desired hemispherical shape to the fabricated disc 94.

In a preferred embodiment, the fabricated disc 94 is placed into the primary cavity 104 of the mold 100. The mold 100 is utilized to form the fabricated disc 94 into the reamer shell 12 of the present invention. The primary mold cavity 104 comprises a plurality of cutouts 108 that are designed to allow room for the tissue cutting surface 44 to bend within. This bending of the tissue cutting surface 44 imparts the desired rake angle 84 into the reamer cutting teeth 80.

As such, the dimensions of the mold cutout 108 feature correlate to the dimensions of the desired reamer cutting features as previously mentioned. In a preferred embodiment, the number of mold cutouts 108 equal the number of rib portions 32. The width 110 of the mold cutout 108 is dimensioned to ensure that the width 38 of the rib portions 32 fit within. In a preferred embodiment, the width 110 of the mold cutout 108 is from about 1 mm to about 20 mm, with a cutout depth 112, ranging from about 5 mm to about 50 mm.

A plurality of mold ridges 114 preferably extends from the primary cavity 104 to the secondary cavity 106. These ridges 114 are designed to provide a barrier which prevents a portion of the reamer cutting surface 44 from progressing further into the space of the cutout 108.

Figure 11:
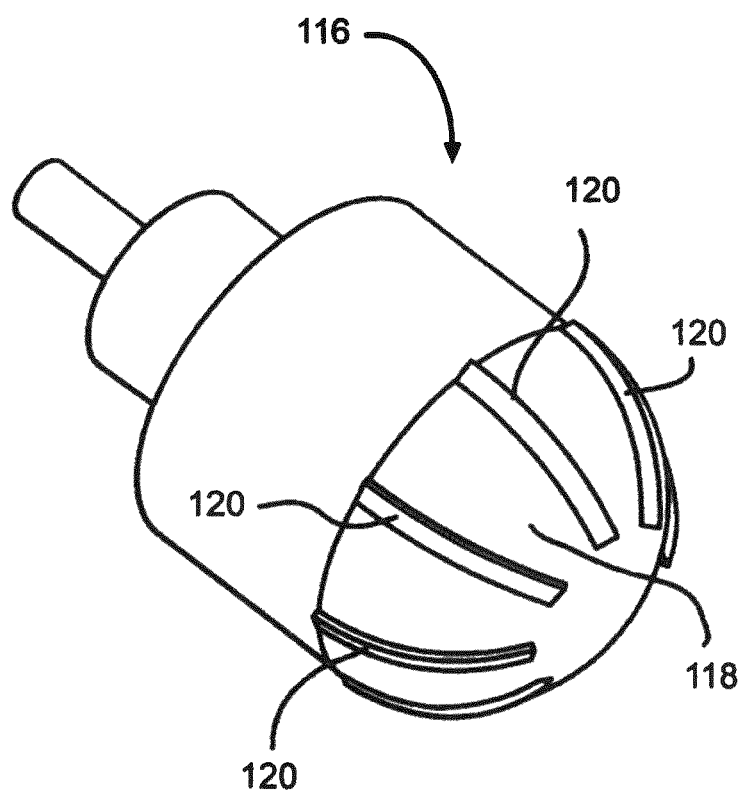
FIG. 11 is a perspective view of a preferred embodiment of a ram 116 used in conjunction with the mold 100 in FIG. 10 for manufacturing the present reamer.

In a preferred embodiment of the present invention, the fabricated disc 94 is initially placed into the primary mold cavity 104 such that the shell rib portions 32 are positioned within the width 110 of the mold cutouts 108. The disc 94 is then pressed into the mold 100 with a ram 116 illustrated in FIG. 11. In a preferred embodiment, ram 116 has a curved bottom surface 118 that is designed to fit within the mold 100. As illustrated, a series of ram ridges 120 extend along a portion of the bottom surface 118 of the ram 116.

The ram ridges 120 are designed to fit adjacent to the mold ridges 114 within the cutouts 108. In a preferred embodiment, the ram 116 is further pressed into the mold 100. As the ram 116 is pressed deeper into the mold 100, the ridges 114 of the ram 116 press against the tissue cutting surfaces 44. Thus, the pressing action of the ram 116 imparts a bend to the cutting surface 44 thereby forming the rake angle 84 into the reamer teeth 80. Therefore, the degree of the rake angle 84 is dependent on the dimensions of both the mold ridge 114 and ram ridge 120. For example, if a greater rake angle 84 is desired, the cutting surface 44 should be bent deeper into the cavity 106.

Thus, it has been shown that the disposable reamer 10 the present invention provides for more efficient tissue removal. The features of the present invention, such as the reamer rib portions 32 with an elongated cutting surface 44, provide an increased tissue cutting surface area which improves tissue removal efficiencies. In addition, the gaps 34 between adjacent rib portions 32 provides a wider opening for debris removal, thus minimizing reamer clogging and further improving tissue removal efficiency. Furthermore, the incorporation of the rake angle 84 increases the tissue removal efficiency of the reamer 10 by allowing the reamer teeth 80 to more efficiently "bite" into tissue.

What is claimed is:

1. A reamer, which comprises:
   a) a cutting shell having a shell curvature comprising at least a portion of a first hemisphere, the cutting shell, extending from an apex shell portion to a lower edge, the cutting shell being rotatable about a longitudinal axis; said cutting shell comprising:
   b) a plurality of rib portions spaced apart from each other by an intermediate gap, each intermediate gap extending from a lower edge of the apex shell portion to the lower edge of the cutting shell, the rib portions having a leading edge and a trailing edge, wherein the leading edge is positioned adjacent the trailing edge of a sequential rib portion;
   c) a tissue cutting surface positioned along a portion of the leading edge, wherein the tissue cutting surface comprises at least two reamer cutting teeth spaced apart by an intermediate notch, each of the notches having a radius of curvature that extends from one cutting tooth to an adjacent cutting tooth, and extends into a width of the rib from the leading edge toward the trailing edge; and
   d) wherein the notch provides two opposing buttress portions of the cutting shell meeting an intermediate cutting edge curvature as an imaginary line segment of a second imaginary hemisphere, the imaginary line segment comprising a continuum of cutting edge radii, each radii originating at a spherical center of the second hemisphere, the second imaginary hemisphere having a greater cross-sectional diameter than and being coincident with the first hemisphere of the cutting shell.

2. The reamer of claim 1 wherein a secondary tissue cutting surface extends along a portion of the trailing edge.

3. The reamer of claim 2 wherein the secondary tissue cutting surface comprises a plurality of reamer cutting teeth spaced apart by a plurality of notches.

4. The reamer of claim 1 wherein the reamer cutting teeth are arranged in a spiral configuration on the cutting shell.

5. The reamer of claim 1 wherein the reamer cutting teeth are positioned at a rake angle from about 5 to about 45.

6. The reamer of claim 1 wherein the tissue cutting surface has a thin razor edge.

7. The reamer of claim 1 wherein a reamer driver interface is attached to the cutting shell, the reamer driver interface comprising a strut and an interface band, wherein the reamer driver interface is constructed such that the interface band encompasses the strut.

8. The reamer of claim 7 wherein a stud secures the interface band to the shell, the stud positioned along an exterior surface of the shell and extends through a width of the cutting shell.

9. The reamer of claim 1 wherein a reamer driver interface comprises a pedestal, a plurality of struts and an interface band attached to the cutting shell; the reamer driver interface constructed such that the interface band encompasses the plurality of struts that extend radially from the pedestal.

10. The reamer of claim 9 wherein a standoff comprises a distal standoff cutting surface and proximal standoff leg portions, wherein the standoff interfaces with the cutting shell and the pedestal such that the distal standoff cutting surface protrudes through a slit in a central region of the reamer cutting shell and the proximal standoff leg portions connect with the pedestal.

11. The reamer of claim 9 wherein the reamer driver interface is connectable to a reamer drive shaft.

12. The reamer of claim 1 wherein the radius of curvature of each of the notches ranges from about 1 mm to about 5 mm.

13. A reamer, which comprises:
   a) a cutting shell having a shell curvature comprising at least a portion of a first hemisphere, the cutting shell extending from an apex shell portion to a lower edge, the cutting shell being rotatable about a longitudinal axis; said cutting shell comprising:
   b) a plurality of rib portions spaced apart from each other by an intermediate gap, each intermediate gap extending from a lower edge of the apex shell portion to the lower edge of the cutting shell, the rib portions having a leading edge and a trailing edge, wherein the leading edge is positioned adjacent the trailing edge of the sequential rib portion;
   c) at least two reamer cutting teeth extending along a portion of the leading edge, the reamer cutting teeth spaced apart by an intermediate notch, each notch having a radius of curvature that extends into a width of the rib from the leading edge toward the trailing edge, and wherein the reamer cutting teeth comprise a cutting edge having a curvature as an imaginary line segment of a second imaginary hemisphere, the imaginary line segment comprising a continuum of cutting edge radii, each radii, originating at a spherical center of the second imaginary hemisphere, the second imaginary hemisphere having a cross-sectional diameter greater than the first hemisphere of the cutting shell; and
   d) a first standoff comprising a first distal standoff cutting surface spaced from a first proximal standoff leg portion, wherein the first standoff interfaces with the cutting shell such that the first distal standoff cutting surface protrudes through a slit in a central region of the reamer cutting shell.

14. The reamer of claim 13 wherein the reamer cutting teeth extend along a portion of the trailing edge.

15. The reamer of claim 13 wherein the reamer cutting teeth are positioned at a rake angle from about 5° to about 45'.

16. The reamer of claim 13 wherein a reamer driver interface is attached to the cutting shell, the reamer driver interface comprising a strut and an interface hand, wherein the reamer driver interface is constructed such that the interface band encompasses the strut.

17. The reamer of claim 13 further including a second standoff comprising a second distal standoff cutting surface spaced from a second proximal standoff leg portion, wherein the first standoff and second standoffs interface together in a perpendicular orientation to form a standoff base.

18. The reamer of claim 17 wherein the first standoff comprises two opposing right and left first standoff leg portions spaced apart by a first archway, a first archway slit positioned through a bottom portion of the first archway, the second standoff comprises two second standoff opposing right and left leg portions spaced apart by a second archway, a second archway slit positioned through a top portion of the second archway, the first archway slit positioned within the second archway slit to form the standoff base.

19. The reamer of claim 13 wherein the first distal standoff cutting surface comprises a series of standoff cutting teeth separated by a series of standoff notches.

20. The reamer of claim 19 wherein a first portion of standoff cutting teeth are oriented about 180° from a second portion of standoff cutting teeth.

21. A reamer, which comprises:
   a) a cutting shell having a shell curvature comprising at least a portion of a hemisphere, extending from an apex to a lower edge, the cutting shell being rotatable about a longitudinal axis; said cutting shell comprising:
   b) a plurality of rib portions, spaced apart by a gap, extending from an intermediate edge, the rib portions having a leading edge and a trailing edge, wherein the leading edge is positioned adjacent the trailing edge of the sequential rib portion, as the shell rotates about the longitudinal axis;
   c) a tissue cutting surface positioned along a portion of the leading edge, wherein the tissue cutting surface comprises a plurality of reamer cutting teeth spaced apart by a plurality of notches, each of the notches having a radius of curvature that extends from one cutting tooth to an adjacent cutting tooth, and extends within a portion of the leading edge; and
   d) wherein each of the reamer cutting teeth are bent outwards from an exterior surface of the cutting shell at a rake angle, each of the reamer cutting teeth extending from the leading edge of a rib portion oriented at about the same rake angle.

22. The reamer of claim 21 wherein the reamer cutting teeth are arranged in a spiral configuration on the cutting shell.

23. The reamer of claim 21 wherein the reamer cutting teeth are positioned at a rake angle from about 5° to about 45'.

24. A reamer, which comprises:
   a) a cutting shell having a shell curvature comprising at least a portion of a first hemisphere, the cutting shell extending from an apex shell portion to a lower edge, the cutting shell being rotatable about a longitudinal axis; said cutting shell comprising:
   b) a plurality of rib portions spaced apart from each other by an intermediate gap, each intermediate gap extending from a lower edge of the apex shell portion to the lower edge of the cutting shell, the rib portions having a leading edge and a trailing edge, wherein the leading edge is positioned adjacent the trailing edge of the sequential rib portion;
   c) at least two reamer cutting teeth extending along a portion of the leading edge, wherein the reamer cutting teeth comprise a cutting edge having a curvature as an imaginary line segment of a second imaginary hemisphere, the imaginary line segment comprising a continuum of cutting edge radii, each radii, originating at a spherical center of the second imaginary hemisphere, the second imaginary hemisphere having a cross-sectional diameter greater than the first hemisphere of the cutting shell;
   d) a first standoff comprising a first distal standoff cutting surface spaced from a first proximal standoff leg portion and a second standoff comprising a second distal standoff cutting surface spaced from a second proximal standoff leg portion, wherein the first and second distal cutting surfaces comprise a series of cutting teeth separated by a series of standoff notches, the first standoff and second standoffs interface together in a perpendicular orientation to form a standoff base, and the first and second standoffs positioned such that the first and second distal standoff cutting surfaces protrude through a slit in a central region of the reamer cutting shell; and e) a reamer driver interface comprising a pedestal, a plurality of struts radially extending from the pedestal, and an interface band, wherein the interface band is attached to the cutting shell by at least one stud that secures the driver interface to the shell; the reamer driver interface constructed such that the interface band encompasses the plurality of struts that extend from the pedestal.

25. The reamer of claim 24 wherein the reamer cutting teeth are arranged in a spiral configuration on the cutting shell.

26. The reamer of claim 24 wherein the reamer cutting teeth are positioned at a rake angle from about 5° to about 45°.

27. A reamer, which comprises:

a) a cutting shell having a shell curvature comprising at least a portion of a first hemisphere, the cutting shell extending from an apex shell portion to a lower edge, the cutting shell being rotatable about a longitudinal axis; said cutting shell comprising:

b) a plurality of rib portions spaced apart from each other by an intermediate gap, each intermediate gap extending from a lower edge of the apex shell portion to the lower edge of the cutting shell, the rib portions having a leading edge and a trailing edge, wherein the leading edge is positioned adjacent the trailing edge of the sequential rib portion;

c) at least two reamer cutting teeth extending along a portion of the leading edge, the reamer cutting teeth spaced apart by an intermediate notch, each notch having a radius of curvature that extends into a width of the rib from the leading edge toward the trailing edge, and wherein the reamer cutting teeth comprise a cutting edge having a curvature as an imaginary line segment of a second imaginary hemisphere, the imaginary line segment comprising a continuum of cutting edge radii, each radii, originating at a spherical center of the second imaginary hemisphere, the second imaginary hemisphere having a cross-sectional diameter greater than the first hemisphere of the cutting shell;

d) a first standoff comprising a first distal standoff cutting surface spaced from a first proximal standoff leg portion and a second standoff comprising a second distal standoff cutting surface spaced from a second proximal standoff leg portion, wherein the first and second distal cutting surfaces comprise a series of cutting teeth separated by a series of standoff notches, the first standoff and second standoffs interface together in a perpendicular orientation to form a standoff base, and the first and second standoffs positioned such that the first and second distal standoff cutting surfaces protrude through a slit in a central region of the reamer cutting shell; and e) a reamer driver interface comprising a pedestal, a plurality of struts radially extending from the pedestal, and an interface band, wherein the interface band is attached to the cutting shell by at least one stud that secures the driver interface to the shell; the reamer driver interface constructed such that the interface band encompasses the plurality of struts that extend from the pedestal.

28. The reamer of claim 27 wherein the reamer cutting teeth are arranged in a spiral configuration on the cutting shell.

29. The reamer of claim 27 wherein the reamer cutting teeth are positioned at a rake angle from about 5' to about 45°.

30. The reamer of claim 27 wherein the radius of curvature of each of the notches ranges from about 1 mm to about 5 mm.

* * * * *

UNITED STATES PATENT AND TRADEMARK OFFICE
CERTIFICATE OF CORRECTION

PATENT NO. : 8,435,243 B2
APPLICATION NO. : 13/025244
DATED : May 7, 2013
INVENTOR(S) : White et al.

It is certified that error appears in the above-identified patent and that said Letters Patent is hereby corrected as shown below:

In the Claims:

Column 10, line 54 delete "5" and "45" and insert --5°-- and --45°--.

Column 11, line 50 delete "45'" and insert --45°--.

Column 11, line 53 delete "hand" and insert --band--.

Column 12, line 36 delete "45'" and insert --45°--.

Column 14, line 31 delete "5'" and insert --5°--.

Signed and Sealed this
Eighteenth Day of June, 2013

Teresa Stanek Rea
*Acting Director of the United States Patent and Trademark Office*